US00PP25202P2

(12) United States Plant Patent
Castorani et al.

(10) Patent No.: US PP25,202 P2
(45) Date of Patent: Dec. 30, 2014

(54) ***SCHIZACHYRIUM* PLANT NAMED 'STANDING OVATION'**

(50) Latin Name: *Schizachyrium scoparium*
Varietal Denomination: Standing Ovation

(71) Applicants: Steven M. Castorani, Hockessin, DE (US); Timothy P McGinty, Lincoln University, PA (US)

(72) Inventors: Steven M. Castorani, Hockessin, DE (US); Timothy P McGinty, Lincoln University, PA (US)

(73) Assignee: North Creek Nurseries, Inc, Landenberg, PA (US)

( * ) Notice: Subject to any disclaimer, the term of this patent is extended or adjusted under 35 U.S.C. 154(b) by 0 days.

(21) Appl. No.: 13/694,121

(22) Filed: Oct. 31, 2012

(51) Int. Cl.
*A01H 5/00* (2006.01)

(52) U.S. Cl.
USPC ..... Plt./384

(58) Field of Classification Search
CPC ..... A01H 5/12
USPC ..... Plt./384
See application file for complete search history.

(56) References Cited

PUBLICATIONS

Stewart, Randy, "Future Plants by Randy Stewart: Blue Stem Grass", filed Jun. 8, 2011, retrieved from the internet at <http://rslandscapedesign.blogspot.com/2011/06/schizachyrium.html> on Jun. 2, 2014, 27 pp.*

* cited by examiner

*Primary Examiner* — June Hwu
*Assistant Examiner* — Louanne Krawczewicz Myer
(74) *Attorney, Agent, or Firm* — Penny J. Aguirre

(57) ABSTRACT

A new cultivar of *Schizachyrium scoparium*, 'Standing Ovation', that is characterized by its wide leaf blades, its foliage that is blue in color with red tips throughout the growing season and changing to red and maroon in fall, and turning brown very late in the season, and its upright and rigid plant habit that is retained without lodging when plants are grown in rich soils or during container production.

2 Drawing Sheets

Botanical classification: *Schizachyrium scoparium.*
Varietal denomination: 'Standing Ovation'.

BACKGROUND OF THE INVENTION

The present invention relates to a new and distinct cultivar of *Schizachyrium scoparium* and will be referred to hereafter by its cultivar name, 'Standing Ovation'. 'Standing Ovation' represents a new cultivar of little bluestem, an ornamental grass grown for landscape use.

The new cultivar, 'Standing Ovation', was discovered by the Inventors as a naturally occurring whole plant mutation in a trail bed in Landenberg, Pa. in summer of 2003. The new cultivar was growing amongst plants of *Schizachyrium scoparium* 'The Blues' (not patented). The parentage is unknown, however 'The Blues' is thought to be a likely parent based on the characteristics of the new cultivar and its proximity.

Asexual reproduction of the new cultivar was first accomplished by one of the Inventors by division in Landenberg, Pa. in May of 2008. Asexual reproduction of the new cultivar by division and tissue culture has shown that the unique features are stable and reproduced true to type in successive generations.

SUMMARY OF THE INVENTION

The following traits have been repeatedly observed over an 8-year period and represent the characteristics of the new cultivar. These attributes in combination distinguish 'Standing Ovation' as a new and unique cultivar of *Schizachyrium.*

1. 'Standing Ovation' exhibits an upright and rigid plant habit.
2. 'Standing Ovation' exhibits wide leaf blades.
3. 'Standing Ovation' exhibits foliage that is blue in color with red tips throughout the growing season and changes to red and maroon in color in fall.
4. 'Standing Ovation' retains it fall color late in the season and does not "brown out" early as is typical of many cultivars of *Schizachyrium scoparium.*
5. 'Standing Ovation' does not lodge when grown in rich soils or when grown in container production.

'The Blues', a likely parent of 'Standing Ovation', differs from 'Standing Ovation' in having narrower blue foliage that does not have red tips or turn red in the fall and that turns brown 6 to 8 weeks earlier in fall and differs in having stems that are thinner and tend to lodge when grown in rich soils or in container production. 'Standing Ovation' can be most closely compared to the cultivars 'MinnblueA' (U.S. Plant Pat. No. 17,310, also known as "Blue Heaven") and 'The Blaze' (not patented). 'MinnblueA' differs from 'Standing Ovation' in having thinner foliage that becomes tinged with red later in the season and turns brown earlier in fall, its taller height, and its tendency to flop in richer soils and during container production. 'The Blaze' differs from 'Standing Ovation' in having thinner leaves that do not turn red until later in the season.

BRIEF DESCRIPTION OF THE DRAWINGS

The accompanying photographs illustrate the characteristics of the new cultivar 'Standing Ovation' and were taken of plants about 3 years in age as grown in trial beds in Landenberg, Pa.

The photograph in FIG. 1 illustrates the plant habit and foliage coloration of 'Standing Ovation' in late October.

Figure 2:
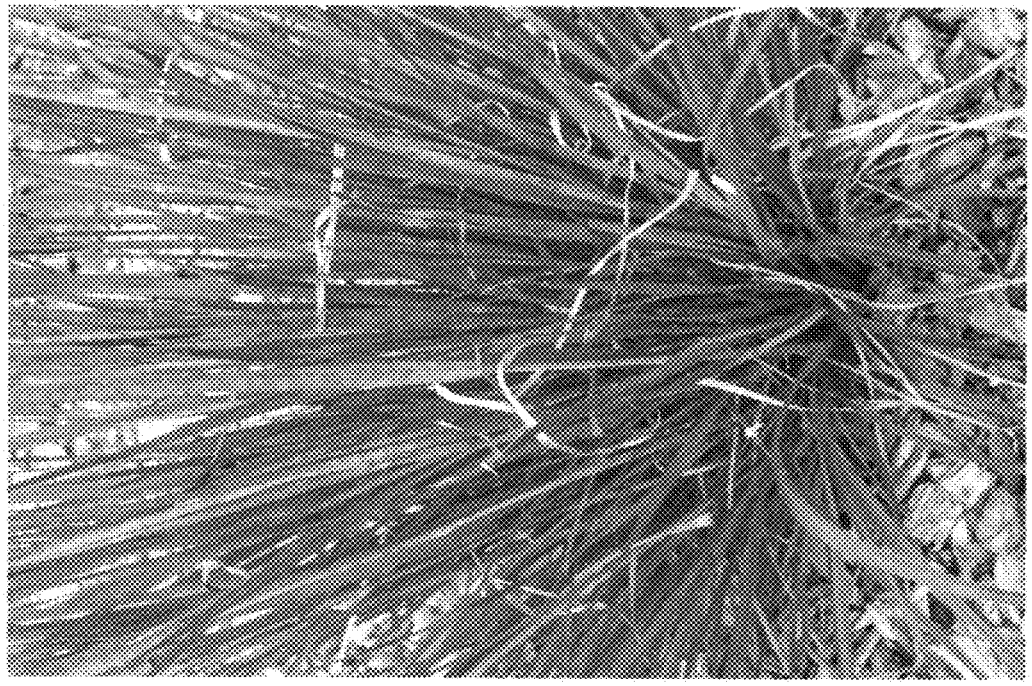
Figure 1:
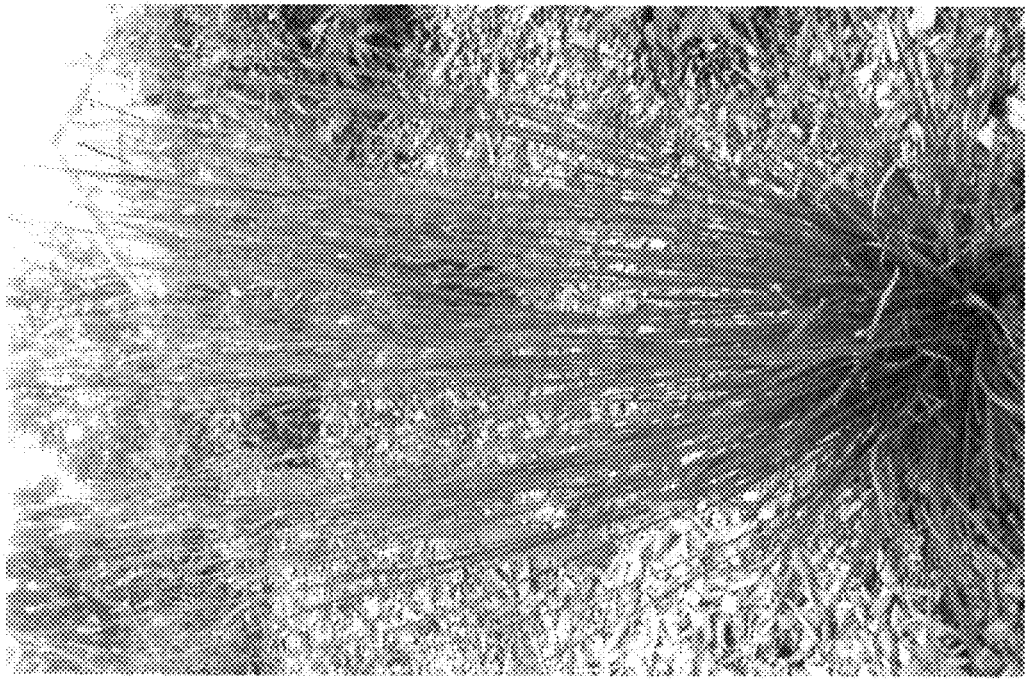

The photograph in FIG. 2 illustrates the foliage coloration of 'Standing Ovation' in early October.

Figure 3:
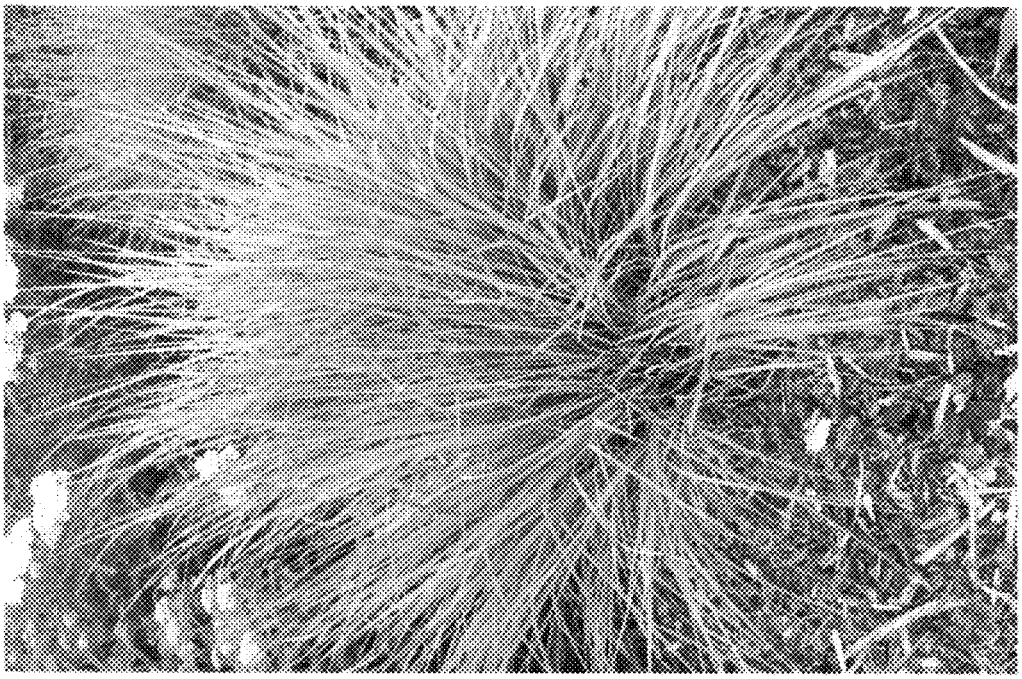

The photograph in FIG. 3 illustrates the foliage coloration of 'Standing Ovation' in summer.

Figure 4:
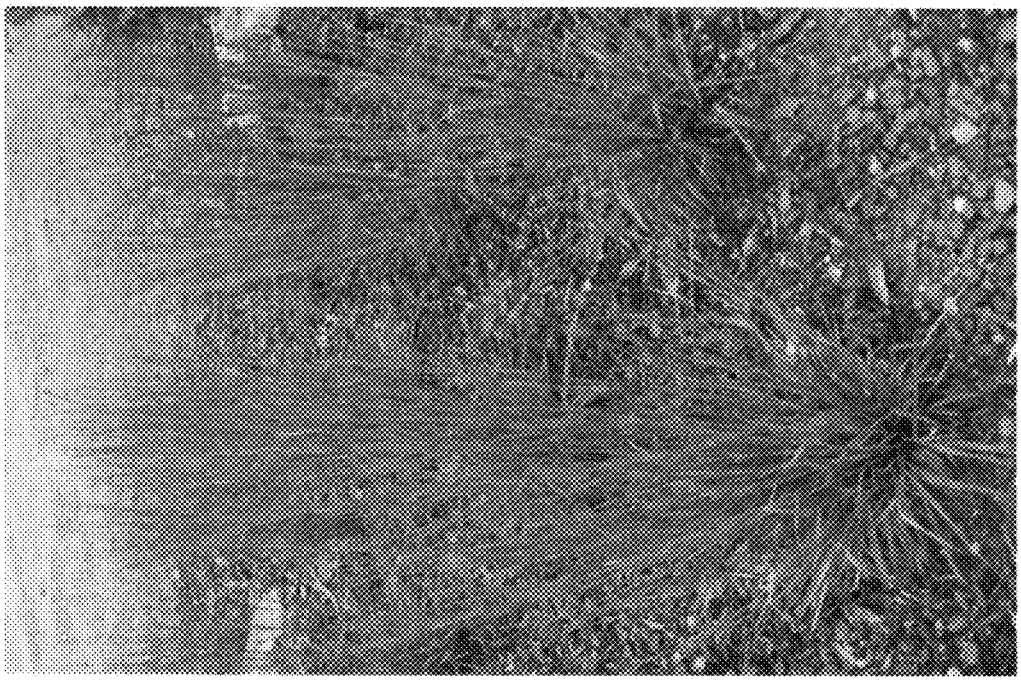

The photograph in FIG. 4 illustrates the foliage coloration of 'Standing Ovation' in November.

The colors in the photographs are as close as possible with the photographic and printing technology utilized. The color values cited in the detailed botanical description accurately describe the colors of the new *Schizachyrium*.

DETAILED BOTANICAL DESCRIPTION

The following is a detailed description of three-year old plants of the new cultivar as grown in Landenberg, Pa. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—From August to February in Pennsylvania.

*Plant habit*.—Herbaceous perennial grass, upright and narrow, thick fine textured foliage.

*Height and width or spread*.—Average of 86 cm in height and 30 cm in width.

*Hardiness zone*.—U.S.D.A. Zones 3 to 9.

*Diseases and pests*.—Has shown moderate rust resistance with less legions than other *Schizachyrium* varieties grown under the same trial conditions.

*Root description*.—Fibrous, wiry, numerous roots, deep.

Growth and propagation:

*Propagation*.—Root division, then basal stem cuttings and tissue culture.

*Growth*.—Vigorous.

Culm (stem) description:

*General*.—Solid, strong, held erect, un-branched with numerous flowering stems emerging from upper portion of culm.

*Culm number*.—An average of 3 per division.

*Culm color* (*non-sheathed portion*).—Early in summer; 145B, late summer/fall; 145B on lower part of culm and 182B or 174B on upper portion of culm.

*Culm size*.—An average of 3 mm in width and up to 100 cm in height from the base of culm to the base of the terminal flowering stem (peduncle), non-sheathed portion between leaves is an average of 3.5 cm in length.

*Culm surface*.—Glabrous.

*Internode length*.—An average of 10 cm.

Foliage description:

*Leaf shape*.—Linear.

*Leaf division*.—Simple.

*Margins*.—Entire, scabrous.

*Leaf base*.—Sheathed to node.

*Leaf venation*.—Parallel, color matches leaf coloration.

*Leaf width*.—Basal leaves; an average of 4 mm, culm leaves; leave blade an average of 6 mm, sheathed portion an average of 3 mm.

*Leaf length*.—Basal leaves; an average of 25 cm, culm leaves; leaf blades an average of 23 cm, sheathed portion an average of 10 cm.

*Leaves number*.—Basal leaves; an average of 6 per division, culm leaves; an average of 5 per culm.

*Leaf surface*.—Glabrous and dull on both surfaces.

*Leaf auricle*.—Not present.

*Leaf collar*.—Continuous around culm, 1.5 mm in height, 145B in color with a coating of 155A.

*Leaf arrangement*.—Alternate, 2 ranked.

*Leaf persistence*.—Foliage dries but persistent through winter.

*Leaf attachment*.—Sheathed.

*Ligule*.—1 mm in width, 161D in color, membranous with about 6 very fine hairs 8 mm in length.

*Leaf color*.—Spring: upper and lower surface 189A, early to late summer upper surface; leaf blades 189A become increasingly suffused with N77A, early to late summer lower surface; leaf blades 189A become slightly suffused with N77A, early to late fall; leaf blades become heavily suffused with a blend of N77A, N79A and N79B on upper surface and a color greyer than N77C on the lower surface, browning does not occur until winter.

Flower description: (Flowers are as typical of *Schizachyrium scoparium*).

*Inflorescent type*.—Racemes at terminus and at nodes.

*Inflorescence no*.—An average of 18 racemes per culm, about 2 to 5 per branch.

*Inflorescence size*.—An average of 5.5 cm in length and 8 mm in diameter (not including peduncle).

*Lastingness of inflorescence*.—About 2 weeks.

*Spikelets*.—An average of 10 per raceme, pair of florets arranged alternately on an articulating rachis; lower floret: pedicellate and sterile; comprised of pedicel about 4 mm in length and 1 mm in. width, 145A in color, surface pubescent with long hairs, and a lanceolate shaped lemma about 3 mm in length and 1 mm in width, 137B in color, with a short awn about 2 mm in length and 145D in color, upper floret; fertile, sessile, comprised to glumes about 6 mm in length and 1.5 mm in width, lanceolate in shape, 137B in color, and glabrous on both surfaces, lemma about 6 mm in length and 1 mm in width, 145D in color with margin 137B, membranous, thin awn about 1.2 mm in length, stamens; 3, about 4 mm in length and 0.7 mm in width, N77A in color, pollen is low in quantity and N199B in color, pistil; 1, 2 stigmas that are quickly fleeting, plumose, about N170D in color and 2 mm in length, ovary; 1, single-celled, about 1 mm in length and width, N170D in color, Rachis. — Articulating, average of 6 cm in length and 0.5 mm in width, a blend of 137B and N199B in color, pubescent surface.

*Peduncle*.—An average of 8 cm in length and 1 mm in width, N77B in color.

*Seed*.—Caryopsis, lemma adhering to the caryopsis, actual caryopsis very small and fine, less than 1 mm in diameter.

It is claimed:

1. A new and distinct cultivar of *Schizachyrium* plant named 'Standing Ovation' as herein illustrated and described.

* * * * *